United States Patent
Jafari et al.

(10) Patent No.: US 6,632,423 B2
(45) Date of Patent: Oct. 14, 2003

(54) VISCOELASTICS FOR USE IN MIDDLE EAR SURGERY

(75) Inventors: Masoud R. Jafari, Arlington, TX (US); Uday Doshi, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 09/857,543

(22) PCT Filed: Mar. 14, 2001

(86) PCT No.: PCT/US01/08064
§ 371 (c)(1),
(2), (4) Date: Jun. 6, 2001

(87) PCT Pub. No.: WO01/68079
PCT Pub. Date: Sep. 20, 2001

(65) Prior Publication Data
US 2002/0169142 A1 Nov. 14, 2002

Related U.S. Application Data

(60) Provisional application No. 60/189,179, filed on Mar. 14, 2000.

(51) Int. Cl.$^7$ .................. A61K 31/795; A61F 13/00; A61F 2/00
(52) U.S. Cl. .................. 424/78.35; 424/422; 424/423
(58) Field of Search .................. 424/94.64, 78.3, 424/422, 423; 514/458

(56) References Cited

U.S. PATENT DOCUMENTS

| | | |
|---|---|---|
| 4,141,973 A | 2/1979 | Balazs |
| 5,166,331 A | 11/1992 | della Valle et al. |
| 5,273,056 A * | 12/1993 | McLaughlin et al. |
| 5,290,552 A * | 3/1994 | Sierra et al. .............. 424/94.64 |
| 5,422,376 A | 6/1995 | Webb |
| 5,501,706 A | 3/1996 | Arenberg |
| 5,811,453 A * | 9/1998 | Yanni et al. ................. 514/458 |
| 5,972,326 A | 10/1999 | Galin et al. |
| 6,051,560 A | 4/2000 | Chang et al. |

FOREIGN PATENT DOCUMENTS

| | | |
|---|---|---|
| EP | 0 341 007 A2 | 11/1989 |
| WO | WO 97/41899 | 11/1997 |
| WO | WO 98/26777 | 6/1998 |
| WO | WO 98/41171 | 9/1998 |

OTHER PUBLICATIONS

Rosiak, et al., "Radiation Formation of Hydrogels for Biomedical Purposes. Some Remarks and Comments," *Radiat. Phys. Chem.* 46(2):161–168 (1995).

Kelly et al., "In Vitro Release Kinetics of Gentamycin from a Sodium Hyaluronate Gel Delivery System Suitable for the Treatment of Peripheral Vestibular Disease," *Drug Dev. Indust. Pharm.* 25(1):15–20 (1999).

Krupala et al., "The Efficacy of Hyaluronic Acid Foam as a Middle Ear Packing Agent in Experimental Tympanoplasty," *Am J Otol*, 19:546–550 (1998).

Laurent et al., "Hyaluronic Acid Reduces Connective Tissue Formation in Middle Ears Filled With Absorbable Gelatin Sponge," *Am. J. Otolaryogol.*, 7(3):181–186 (1986).

Merchant et al., "Current Status and Future Challenges of Tympanoplasty," *Eur Arch Otorhinolaryngol*, 255:221–228 (1998).

Poyer et al., "Quantitative Method to Determine the Cohesion of Viscoelastic Agents by Dynamic Aspiration," *J. Cataract Refract. Surg.*, 24:1130–1135 (1998).

* cited by examiner

*Primary Examiner*—Thurman K. Page
*Assistant Examiner*—Blessing Fubara

(57) ABSTRACT

Disclosed are viscoelastic compositions and methods of their use in surgical and non-surgical packing and in effecting drug delivery, especially in conjunction with trauma to of disorders of the ear.

18 Claims, 2 Drawing Sheets

VISCOELASTICS FOR USE IN MIDDLE EAR SURGERY

This application is a 371 of PCT/US01/08064 filed on Mar. 14, 2001 which claims benefit of provisional application of 60/189,179, filed on Mar 14, 2000.

BACKGROUND OF THE INVENTION

The present invention relates to the use of viscoelastics, typically in surgery, to prevent or reduce unwanted tissue adhesion and/or fibrosis subsequent to the trauma or surgical insult. The methods of the present invention are particularly useful in the field of otic therapy, and especially in therapies associated with the treatment of middle ear conditions which arise as a consequence of disease, injury, surgery and the like. The compositions and methods of the present invention are particularly useful in mastoidectomy and tympanoplasty surgeries. In addition, the compositions of the present invention may be used as a packing agent, with or without a therapeutic agent, for the management of otitis external in the external ear canal.

The human ear consists of a series of three compartments: the external, middle and inner ears. These are grossly depicted in FIG. 1. The external ear, which consists of the cartilaginous outer ear and the external canal are designed to gather sound and protect the tympanic membrane, which marks the beginning of the middle ear. The middle ear is an air filled compartment having three principle structures: (1) the tympanic membrane; (2) the ossicular chain (consisting of the incus, malleus, and stapes); and (3) the eustachian tube. The tympanic membrane and ossicular chain function to convert sound waves passing through the external cannel into mechanical vibrations which can then be processed by the inner ear. The eustachian tube functions as a pressure equalizer to avoid undue strain on the tympanic membrane. The inner ear consists of the cochlea and the vestibular apparatus. The "snail shell" shaped cochlea contains sound receptor cells, which respond to the sound vibrations and send signals to the brain. It is these signals that are responsible for the sound being "heard." The vestibular apparatus of the inner ear operates in a similar fashion, but deals with balance and motion, rather than sound.

Of the three ear compartments, the middle ear is perhaps the most prone to trauma which can result in loss of hearing. One reason for this is that the tympanic membrane and the ossicular chain are extremely delicate. Any trauma which impedes or alters the motility of the respective components will necessarily impact the transducer function they serve. The three tiny bones of the ossicular chain and reconstructions thereof are particularly susceptible to impaired function if the ossicular chain is permitted to collapse before it is sufficiently healed. Such collapse can result in undesirable adhesions and fibrosis that can severely limit the motility of the ossicular chain members and hence their ability to serve the transducer function. In order to stabilize the tympanic membrane and the ossicular chain, at the end of middle ear surgery, the middle ear compartment is typically "packed" with some type of gel product.

Several such products are known. Absorbable gelatin sponge (AGS) (Gelfoam™) with or without Gelfilm™— (both of Pharmacia Corp., Kalamazoo, Mich., U.S.A.) have been used as supportive aids in the middle ear. One drawback to the use of these products is the relatively difficult "cut to fit" technique that must be employed by the surgeon to effect the packing. Also, although used extensively in middle ear surgery, AGS has been implicated as a possible factor in the development of unexpected adhesions and new bone formation. Other attempts have been made to improve the supportive properties of these packing materials. Hyaluronic acid (A) foam (Genzyme Corporation, Cambridge, Mass., U.S.A.) has also been tested, but has shown only marginal benefits over conventional packing. Krupala et al., *Am J Otol* 19:546–550 (1998). "The degree of adhesion was similar for both groups [AGS and HA foam]." Id. at 549. Rapid elimination of conventional HA solutions through the Eustachian tube may limit its capability to provide adequate graft support, leading to adhesion formation. Laurent et al., *Hyaluronic acid reduces connective tissue formation in middle ears filled with absorbable gelatin sponge, Am. J. Otolaryogol.,* 7(3):181–186 (1986). Krupata et al. have suggested that such elimination can be avoided by plugging the eustachian tube with gelatin sponge. Id. at 546. This approach, however, appears not to be ideal as it requires two separate packing materials.

Merchant et al., *Current status and future challenges of tympanoplasty, Eur Arch Otorhinolaryngol,* 255:221–228 (1998), discuss the deficiencies of currently available therapies in terms of middle ear adhesions and fibrosis:

Proliferation of fibrous tissue and the formation of adhesions are significant problems that are more prone to occur when the middle ear mucosa is diseased, removed, or traumatized. Many different materials have been placed in the middle ear in an attempt to prevent formation of adhesions and fibrous tissue. These materials include absorbable gelatin sponge (Gelfoam), hyaluronic acid. Silastic and Teflon, Gelfoam elicits a host inflammatory response leading to its resorption [citations omitted]. In some cases, this inflammatory response results in adhesions, especially when the middle ear mucosa is deficient. Further, gelfoam is resorbed within 2 weeks, which is probably insufficient time for mucosal regeneration to occur. Hyaluronic acid is somewhat more difficult to handle than gelfoam [citation omitted] and is also absorbed before mucosal regeneration is likely to be completed. Silastic and Teflon sheeting are relatively inert [citations omitted] but they are not resorbed and can extrude on occasion. In some cases, Silastic and Teflon become engulfed by fibrous tissue leading to a nonaerated ear [citation omitted]. Hence, none of the currently available spacer materials is ideal. What is needed is a material that will remain in place for several weeks to allow sufficient time for mucosal regeneration and will then undergo degradation and resorption so that the ear can become aerated without fibrosis.

Surgical grade viscoelastics are known in the art. Several ophthalmic viscoelasltics are commercially available: VISCOAT®, PROVISC®, CELLUGEL® and DUOVISC® (Alcon Laboratories, Inc., Fort Worth, Tex., U.S.A.); HEALON® and HEALON GV® (Pharmacia Corp., Kalamazoo, Mich., U.S.A.); OCUCOAT®, AMVISC®, and AMVISC® PLUS (Bausch & Lomb Surgical, Claremont, Calif., U.S.A.); and VITRAX® (Allergan, Irvine, Calif., U.S.A.).

It is also known that certain viscoelastics may serve as carriers or drug delivery devices for pharmacologically active substances. See, e.g. U.S. Pat. No. 5,166,331. Kelly et al., *In vitro release kinetics of gentamycin from a sodium hyaluronate gel delivery system suitable for the treatment of peripheral vestibular disease, Drug Dev. Indust. Pharm.* 25(1):15–20 (1999), disclose in vitro testing of a delivery system comprising gentamycin in a sodium hyaluronate gel for the treatment of peripheral vestibular disease. World Patent No. WO 98/41171 entitled "Controlled Release of Pharmaceuticals in the Anterior Chamber of the Eye" relates to compositions which maintain structural integrity of the anterior chamber of the eye during ophthalmic surgery and thereby protect anterior segment tissues while providing sustained delivery of drugs (e.g., miotics, mydriotics or anesthetics). The ocular surgical use of viscoelastic agents having different cohesive properties is disclosed in U.S. Pat. No. 5,273,056. Prior art viscoelastics, however, are not known to be particularly well-suited for use as a middle ear packing material, for the aforementioned reasons.

SUMMARY OF THE INVENTION

Figure 1:
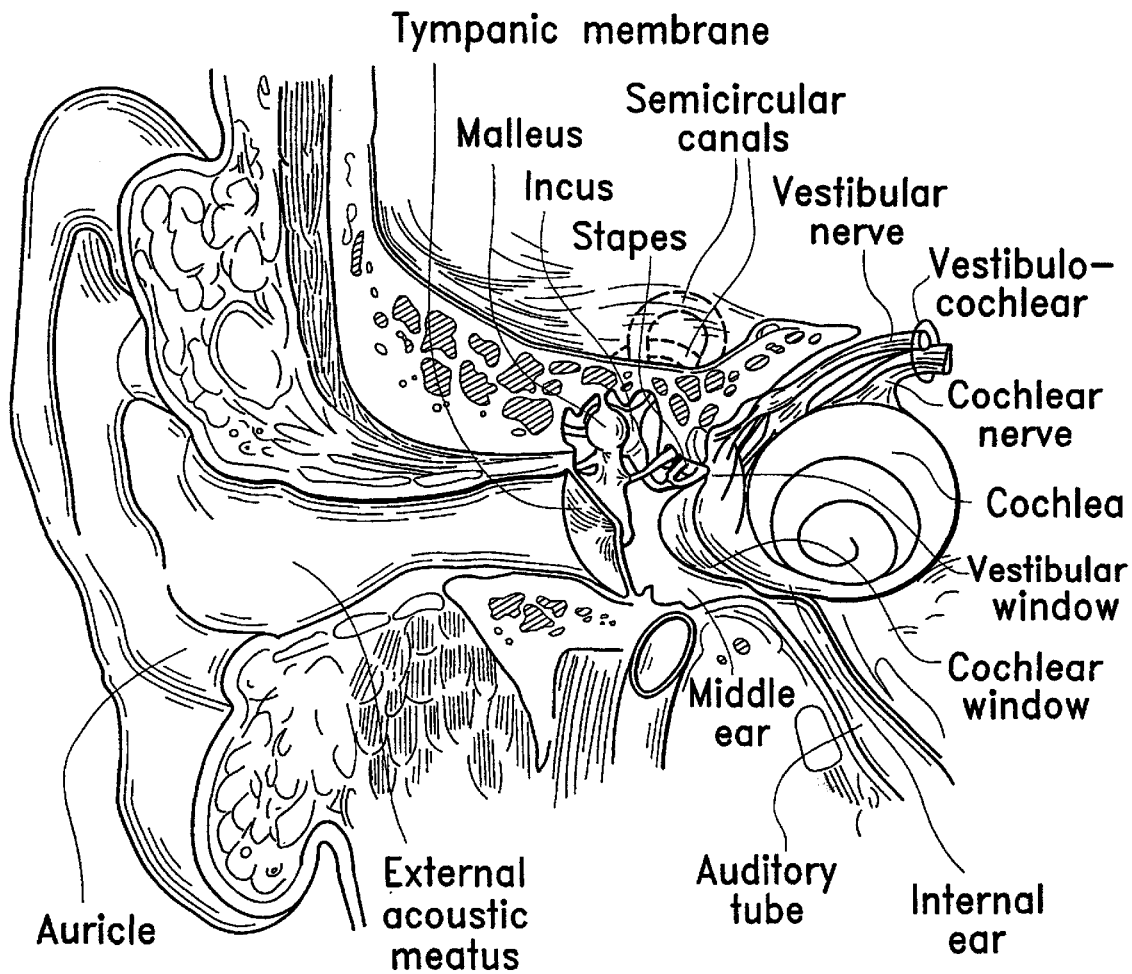
FIG. 1 is a cross-sectional depiction of the anatomy of the human ear.

It has now been discovered that certain highly viscous viscoelastic materials with superior cohesive/dispersive properties have significantly improved packing characteristics for use in both the middle ear and external ear canal. The packing materials of the present invention provide adequate support for otologic repair until adequate healing can take place. These materials are less susceptible to premature bioabsorption or degradation than those previously used in the art, are therefore suitable for enhanced drug delivery, if desired, and will promote healing with minimal tissue fibrosis. It has been discovered that viscoelastic materials used for tissue separation/manipulation in middle ear surgery should be retained in the ear for up to three weeks, preferably for one to two weeks, and should not induce fibrosis. It has further been discovered that viscoelastics suitable for such purposes will have certain physical characteristics, including high viscosity and a suitable cohesion-dispersion index. These same physical characteristics are desirable in viscoelastics being employed for packing the external ear canal. Any physiologically acceptable viscoelastic formulated to meet the inventive physical characteristic requirements will be suitable for purposes of the present invention.

DETAILED DESCRIPTION OF THE INVENTION

The middle ear is part of a continuous pathway that runs from the nose and throat through the eustachian tubes to the middle ear, and then to the surrounding mastoid air cells in the bone and cartilage surrounding the ear. Infection can easily travel along this pathway to the middle ear and to the mastoid air cells when infected, the chambers in the middle ear and mastoid air cells fill with fluid. The fluid creates pressure causing pain and temporary hearing loss. If such infections are not resolved, the middle ear structures can become permanently damaged. Ear pathologies associated with perforation or a conductive deficit include but are not limited to: otitis media, otitis externa, granulation tissue, and trauma (including without limitation myringotomy). Other, non-perforation disorders include but are not limited to: tympanosclerosis, otosclerosis, congenital cholesteatoma, and eustachian tube dysfunction.

It has now been discovered that the suitability of a viscoelastic material for use as packing agent for surgeries involving delicate tissues or a significant risk of undesirable adhesions or fibrosis as, for example, middle ear surgery, is not dependent on a single physical characteristic of the viscoelastic material, but rather a combination of characteristics. Key characteristics of the suitable viscoelastic material are viscosity and cohesion-dispersion index (CDI). The zero shear viscosities of many viscoelastics are known in the literature and may, in any event, be determined by means well known in the art. For present purposes, zero shear viscosity was determined using a Bohlin CS Rheometer as more particularly described in the following examples.

Surgical grade viscoelastic agents are known in the art, especially as adjuncts in ophthalmic surgeries. Methods of purifying and sterilizing such viscoelastic agents are described in U.S. Pat. Nos. 4,141,973 and 5,422,376, and 6,051,560, all of which are by this reference incorporated herein. It is also known that viscoelastic agents may be used as carriers for pharmacologically active agents. See, e.g., U.S. Pat. Nos. 5,811,453 and 5,972,326, the contents of both of which are by this reference incorporated herein.

Viscoelastic agents which are useful for methods of the present invention include but are not limited to: modified or unmodified sodium hyaluronate, chondroitin sulfate, polyacrylamide, carbomers, HPMC, polyvinylpyrrolidone, proteoglycans, collagen, methylcellulose, carboxymethyl cellulose, ethylcellulose, and keratin of various molecular weights, or combinations thereof. In addition, mucoadhesive polymers (for example, polyglycols (hydrogels), chitosan, polycarbophil, hydroxyethyl cellulose, and poloxamer) may be added to the foregoing viscoelastics to enhance dispersivity and thereby prolong retention time at the desired site, for example, in the middle ear cavity or in the external canal.

Viscoelastics exhibit a degree of cohesion, which is the result of intermolecular entanglement. A high degree of cohesion imparts a bolus-like behavior to the viscoelastic agent. While not dependent on any particular theory, the present invention recognizes that the relative cohesion of a viscoelastic agent may affect the degree to which it is prematurely evacuated from the desired site, and particularly from the middle ear cavity through the eustachian tube. The more cohesive the agent, the more likely it is to be prematurely removed. The less cohesive (i.e. more dispersive) the agent provided it possesses sufficient viscosity), the more likely it is to remain in a desired location, such as the middle ear cavity, for a sufficient time to allow adequate healing The viscosity and CDI of the viscoelastics of the present invention are balanced to meet this objective. Surprisingly, it has been discovered that these viscoelastics are remarkably effective at preventing undesirable tissue-tissue adhesions and fibrosis. The said viscoelastics are preferably used therefore as a packing agent in the middle ear and/or the external ear canal.

A further object of the present invention is to provide a method for treating traumatized tissue, and especially ear disorders, using the viscoelastics described herein. Specifically, the viscoelastics of the present invention may be used as a delivery vehicle for therapeutic agents useful in treating a variety of otic conditions, including those enumerated above. The viscoelastics, containing one or more therapeutic agents, may be instilled during or upon completion of a surgical procedure, and especially in conjunction with middle ear surgery where antibiotics and anti-inflammatory agents are preferred therapeutic agents. They may also be used in non-surgical procedures. The external canal may be treated by packing it with the viscoelastic containing the therapeutic agent(s). The middle ear can similarly be treated by i) applying such viscoelastic to the tympanic membrane where the therapeutic agent will cross the membrane into the middle ear, or, ii) in a more aggressive regimen, injecting it through the tympanic membrane into the middle ear. Even treatment of the inner ear, which is not readily accessible by conventional surgical procedures, may also be effected using the viscoelastics of the present invention for drug delivery. Contacting the membrane of the oval window separating the middle and inner ear with such viscoelastics will effect delivery of the drug across the membrane and into the inner ear. Such contact may be effected by packing the middle ear, for example in conjunction with surgery, or by the targeted application of the viscoelastic to the oval window, for example by spraying a coating of the viscoelastic on the target site. Among anti-inflammatory agents, particularly well-suited for such trans-membrane applications are the compounds described in U.S. Pat. No. 5,475,034, the contents of which are by this reference incorporated herein. In most instances, the extended retention of the viscoelastics on the target tissue, which is attributable to their viscosity and CDI characteristics, will permit more drug to reach the target tissue over a longer period of time and with a lower dose than would be possible using conventional approaches.

Several physical parameters of viscoelastic materials have been measured and are well-documented including viscosity, pseudoplasticity (shear-thinning), and molecular weight. A method to measure their cohesion is described by Poyer et al., *Quantitative method to determine the cohesion of viscoelastic agents, by dynamic aspiration*, J. Cataract Refract. Surg., 24:1130–1135 (1998), the contents of which are by this reference incorporated herein. Poyer et al. describe a cohesion-dispersion index (CDI) for viscoelastics which is determined in a manner generally depicted in FIG. 2 and using the following materials and methods.

MATERIALS AND METHODS

Materials and Equipment

Polypropylene test tubes (found bottom, 14 mL) were obtained from Becton Dickinson Labware and polypropylene pipette tips (model RT-20), from Rainin Instrument Co. Cell culture clusters (24 well) were purchased from Costar. A Sartorius model 1612 balance was used for the gravimetric determinations and a positive displacement pipette (Rainin model M1000), for viscoelastic sample transfer. Vacuum was applied with a Gast vacuum pump.

Aspiration of Viscoelastic Sample

Figure 2:
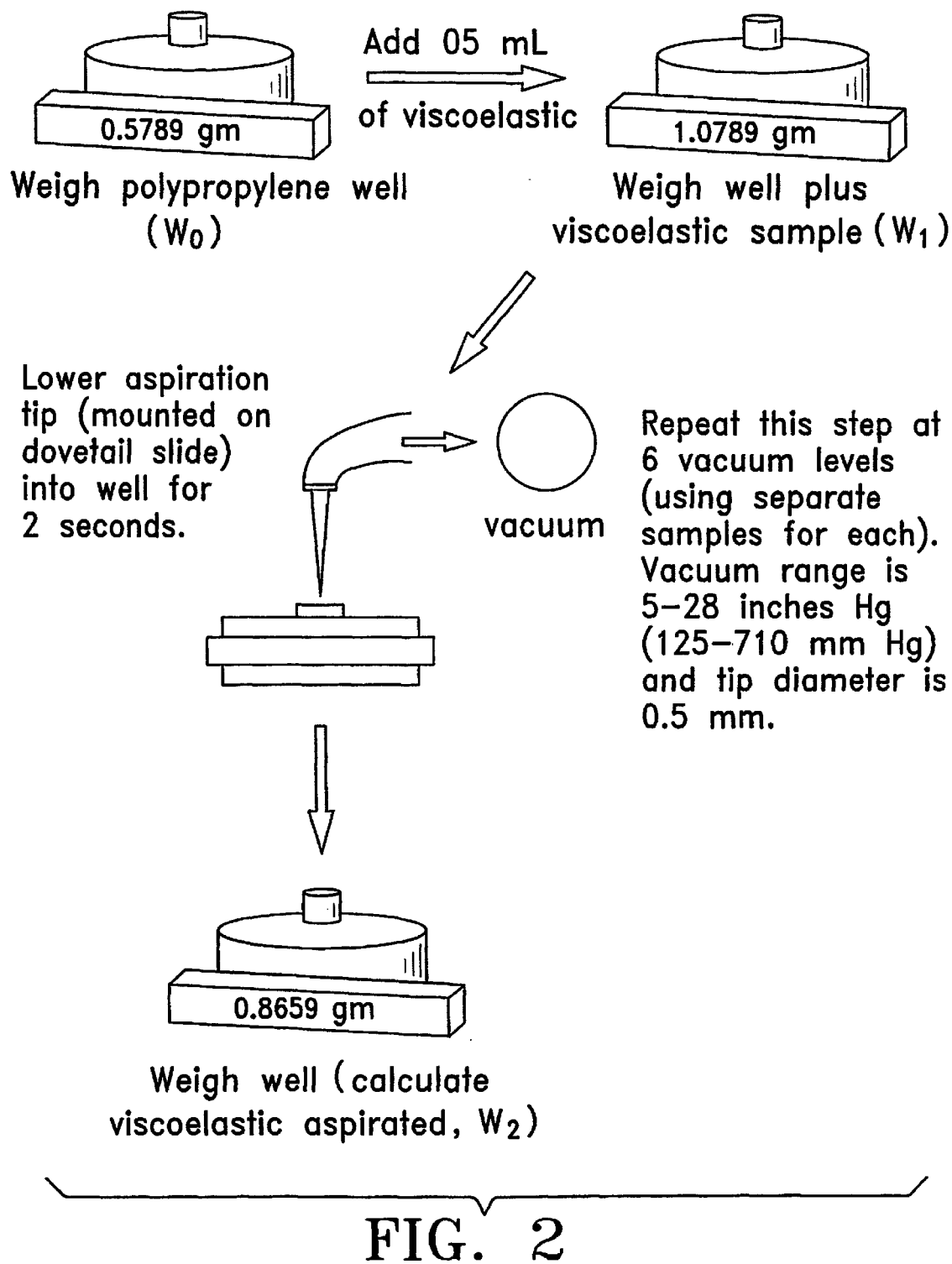
FIG. 2 is a diagram depicting method of cohesion-dispersion determination.

Polypropylene well inserts were cut from the bottom of 14 mL test tubes, weighted ($W_0$), and inserted into the well of a 24-well cell culture cluster for secure holding (FIG. 2). Polypropylene provides a non-adsorptive surface to minimize interference with aspiration by potential adsorptive forces from the container. The viscoelastic sample (0.5 mL) was dispensed into the insert with a positive displacement pipette and the insert (containing sample) reweighed ($W_1$).

A regulated vacuum was connected via flexible polyvinylchloride tubing to a polypropylene pipette tip (internal diameter 0.5 mm). Vacuum was applied at various levels indicated by a gauge (5, 10, 15, 20, 24, and 28 inches Hg, equivalent to 127, 254, 381, 508, 610, and 711 mm Hg) to the viscoelastic samples, using a new sample (in duplicate) for each vacuum level. Vacuum was applied with the pipette tip held in the clamp of a dovetail slide. The tip was lowered into the sample for a contact time of 2 seconds. The tip's position was fixed at an angle of 80 degrees from the horizontal surface of the sample, preventing obstruction of the tip by the bottom of the insert. After aspiration was performed for each sample, all inserts were reweighed ($W_2$).

Data and Statistical Analysis

The percentage of the viscoelastic sample aspirated was calculated as follows:

$$\% \text{ Aspirated} = \frac{(W_1 - W_2)}{(W_1 - W_0)} \times 100\%$$

Data were plotted as percentage aspirated versus vacuum. the slopes of the steepest portion of the curve for each viscoelastic (based on the 2 steepest points of the curve) were compared for statistical significance using covariance analysis (SAS Institute, Inc.). The value of each slope represents the CDI of a particular viscoelastic agent (percentage aspirated/100 mm Hg vacuum).

The break point of a viscoelastic agent represents the vacuum level at which bolus removal of the agent begins. Bolus removal (for the purpose of break point) is defined as having more than 25% of the sample removed by a single vacuum level. Break point was determined using the percentage aspirated versus vacuum curves. Dispersive viscoelastic agents tend to have a low break point and cohesive compounds, a relatively high break point (indicative of sudden bolus removal).

Using the foregoing methodologies to determine a viscoelastic agent's viscosity and CDI, we have defined a Retention Factor (R) by the following formula:

$$R = V_0 \times CDI$$

where $V_0$ is the zero shear viscosity in Pa.s and CDI is as defined above. The present invention is directed to viscoelastic agents that are sufficiently viscous to support delicate tissue, including, e.g., the ossicular chain, and are sufficiently dispersive to avoid premature evacuation from the instillation site via, e.g., the eustachian tube. More specifically, the invention is directed to viscoelastic agents optionally combined with one or more mucoadhesive polymers (hereinafter "viscoelastic compositions"), for which the Retention Factor is at least 600 and preferably greater than 600 (i.e. R>600); wherein such viscoelastic compositions have a zero shear viscosity ($V_0$) greater than 30 Pa.s, preferably greater than 50 Pa.s, and most preferably between about 100 Pa.s and 8000 Pa.s; and wherein the CDI for such viscoelastic compositions is less than 20, preferably less than 10, and most preferably between about 2 and 7.

More detailed aspects and embodiments of the present invention are provided in the following examples.

EXAMPLE 1

HPMC Solution

Highly Viscous Solution

| Ingredient | % w/v |
| --- | --- |
| HPMC (E4M-K100M) | 2 to 8 |
| Calcium chloride | 0.048 |
| Sodium chloride | 0.525 |
| Potassium chloride | 0.075 |
| Magnesium chloride | 0.030 |
| Sodium Citrate | 0.170 |
| Sodium acetate | 0.390 |
| HCl/NaOH | Adjust pH |
| WFI | QS 100% |

EXAMPLE 2

Highly Viscous Sodium Hyaluronate Solution

Use of High Molecular Weight HA with Intrinsic Viscosity of 25–38 dl/g

| Ingredient | % w/v |
| --- | --- |
| Na Hyaluronate | 1–5 |
| Dibasic Sodium Phosphate | 0.056 |
| Monobasic sod. phosphate | 0.004 |
| Sodium Chloride | 0.840 |
| HCl/NaOH | Adjust pH |
| WFI | QS 100% |

EXAMPLE 3

| Ingredient | % w/v |
| --- | --- |
| HPMC (E4M-K100M) | 2 to 8 |
| Mitomycin C | 0.01–0.1 |
| Calcium chloride | 0.048 |
| Sodium chloride | 0.030 |
| Sodium Citrate | 0.170 |
| Sodium acetate | 0.390 |
| HCl/NaOH | Adjust pH |
| WFI | QS 100% |

EXAMPLE 4

| Ingredient | % w/v |
| --- | --- |
| Na Hyaluronate | 1–5 |
| Mitomycin C | 0.01–0.1 |
| Dibasic Sodium Phosphate | 0.056 |
| Monobasic sod. phosphate | 0.004 |
| Sodium Chloride | 0.840 |
| HCl/NaOH | Adjust pH |
| WFI | QS 100% |

EXAMPLE 5

| Ingredient | % w/v |
| --- | --- |
| HPMC (E4M-K100M) | 2 to 8 |
| Compound A | 0.00005–0.005 |
| Cremophore EL | 0.25–2.5 |
| Sodium Acorbate | 0.01–1.0 |
| Calcium chloride | 0.048 |
| Sodium chloride | 0.030 |
| Sodium Citrate | 0.170 |
| Sodium acetate | 0.390 |
| HCl/NaOH | Adjust pH |
| WFI | QS 100% |

EXAMPLE 6

| Ingredient | % w/v |
| --- | --- |
| Na Hyaluronate | 1–5% |
| Compound A | 0.00005–0.005 |
| Cremophore EL | 0.25–2.5 |
| Sodium Acorbate | 0.01–1. |
| Dibasic Sodium Phosphate | 0.056 |
| Monobasic sod. phosphate | 0.004 |
| Sodium Chloride | 0.840 |
| HCl/NaOH | Adjust pH |
| WFI | QS 100% |

Other Antifibrotic Compounds can be included in place of Mitomycin C in EXAMPLES 3 and 4. A list commonly used antifibrotics and proposed concentrations are included below.

| | |
| --- | --- |
| Mitomycin C | 0.01–0.1% |
| 5 Fluorouracil (5-FU) | 2–8 % |
| Taxol | 0.002–0.01% |
| Etopposide | 0.05–0.15% |

In the above example; Compound A is 2-(6-hydroxy-2,5,7,8-tetramethyl-3,4-dihydro-2H-benzo[1,2-b]pyran-2-(6-methoxy-2-naphthyl)propionate; the sodium hyaluronate (Genzyme Corporation, Cambridge, Mass., U.S.A.) had a molecular weight of approximately 2.2 million Daltons; the chondroitin sulfate (SKK, Japan) had a molecular weight of approximately 50,000 Daltons; the BPMC (Colorcon) had a viscosity grade of K100M; and the carbopol (B. F. Goodrich) had a viscosity grade of 940.

EXAMPLE 7

The following formulations in Table 1 were considered for evaluations in the middle ear surgery.

TABLE 1

Otic VE formulations evaluated in Gerbil Model

| Formulation# | Description |
| --- | --- |
| 1 | 1.6% HMW HA in Viscoat Buffer |
| 2 | 1.6% HMW HA + 4% CS in Viscoat Buffer |
| 3 | Carbopol (940) 2% w/v in PBS |
| 4 | HPMC (K100M) 2.5% w/v in PBS |

The goal of this study was to examine viscoelastic products in terms of duration in the middle ear, ototoxicity risk, and possible sources of fibrosis.

Methods: 34 Mongolian gerbils underwent a combination of preoperative audio brainstem response (ABR) threshold analysis, simple mastoidectomies, and post operative ABR's to evaluate the above stated goals. All animals were carefully anesthetized per previously published protocols. Animals for the fibrosis study underwent bilateral surgeries with product in one ear and none in the other. animals for ototoxicity studies underwent implantation of the product bilaterally with postoperative threshold determinations once all product had migrated out of the middle ear. Animals used to determine duration of the product in the middle ear were examined at both 7 and 14 days postimplantation and amount of material in the ear was determined by otomicroscopic exam and reopening of the ear when necessary.

Results: Of the products tested, one product, product 2, clearly represented a superior product in terms of duration in the middle ear. This product remained in the ear at one week in 7/8 ears and was totally gone by 14 days examination. The other products showed less encouraging results. In terms of ototoxicity, all products tested showed no shift in ABR thresholds. Fibrosis studies initially showed no evidence of increased levels of fibrosis versus control ears.

Conclusion: These products are not ototoxic, remain in the middle ear for a predictable amount of time, and initially show no evidence of a propensity to cause fibrosis in the middle ear mucosa.

EXAMPLE 8

The summary of the results with respect to rheology and cohesivity for 4 formulations is presented in Table 2. The cohesion-dispersion index ("CDI") was determined in accordance with the methodology of Poyer et al., "Quantitative method to determine the cohesion of viscoelastic agents by dynamic aspiration", *J. Cataract Refract Surg*, 24:1130–1135 (1998).

TABLE 2

Otic VE Formulations Rheology and Cohesivity

| Product | Viscosity (Pa.s) | CDI[a] | Retention (Days) | Retention Factor[b] |
|---|---|---|---|---|
| 1.6% HA | 1800 | 75 | <7 | 135,000 |
| 1.6% HA + 4% CS | 3000 | 5 | 7–14 | 115,000 |
| HPMC 2.5% | 100 | 6 | <7 | 600 |
| Carbopol 2% | 500,000 | 7 | <7 | 3,500,000 |

[a]Percent viscoelastic aspirated per 100 mm Hg vacuum
[b]Product of viscosity and CDI Viscosity is zero shear viscosity and was determined using a Bohlin CS (Controlled Stress) Rheometer (Bohlin Rheologic AB, Lund, Sweden—Asset No. 17627)), equipped with Bohlin Software 5.4, an HP Color DeskJet 1600C printer, and VWR Programmable water bath Model 1147 (Alcon Asset No. 100483). Measurements were made at 25° C. (±0.5° C.). The cone plate was cleaned between each measurement. Measuring system: A 4° cone and 40-mm diameter plate, CP 4/40 set at a gap width of 0.15 mm. The rheology experiment consists of stress viscometer. Shear stresses between 0.06 and 596 Pa were applied. The corresponding shear rate and viscosity were calculated after 100 seconds (integration time) or wherever the system approached steady state, >0.98. Measurement interval 10 sec. with constant delay time of 10 sec.

The formulations were designed to have a wide array of highly cohesive to dispersive material in terms of evaluating the product's retention and coatability of the surrounding tissues. Formulations were made in low, intermediate and high viscosity. As indicated above, formulation 2 (1.6% HMW HA+4% CS) was found to be superior in terms of retention to the other evaluated formulations. Retention times in excess of 14 days may be obtained by adding the mucoadhesive Carbopol (for example the 2% gel) to the HA and/or CS polymers.

Those skilled in the art will appreciate that the compositions and methods of the present invention will have utility in a variety of therapies and especially in drug delivery and reconstructive surgery. The present invention offers sustained, long-duration drug delivery and is particularly well suited for delivery of anti-fibrotics, antibiotics, steroidal and non-steroidal antiinflammatories, anesthetics, analgesics and other medicaments or gene therapies to the middle and inner ear. The presently disclosed compositions and methods may also be used in any environment where there is a need for tissue separation or stabilization and the potential exists for complications, typically post-surgical, arising from tissue fibrosis and/or adhesions. They will be particularly useful in nasal, spinal cord, cardiovascular, orthopoedic and orthodontic surgical procedures that would otherwise be prone to such complications. Skilled practitioners will recognize that the preferred retention characteristics of the viscoelastic agent will depend upon the type of procedure for which it is being employed. Using the present teaching, retention characteristics can be optimized for a specific function or type of procedure. As used herein, the term "pharmaceutically acceptable vehicle" means any vehicle that would be suitable for therapeutic administration of a viscoelastic agent or a therapeutic agent to a patient by any conventional means without significant deleterious health consequences. An aqueous vehicle is most preferred.

The invention has been described by reference to certain preferred embodiments; however, it should be understood that it may be embodied in other specific forms or variations thereof without departing from its spirit or central characteristics. The embodiments described above are therefore considered to be illustrative in all respects and not restrictive, the scope of the invention being indicated by the appended claims rather than by the foregoing description.

What is claimed is:

1. A method of inhibiting or reducing fibrosis and/or adhesion in traumatized tissues, comprising the administration of a tissue stabilizing effective amount of a viscoelastic agent to the traumatized tissue, wherein said agent is characterized by a viscosity ($V_o$) of at least 30 Pa.s, and a cohesion-dispersion index (CDI) greater than zero and less than 20, such that the product of said viscosity and cohesion dispersion index afford a retention factor (R) of at least 600 in accordance with the formula:

$$V_o \times CDI \times R;$$

and wherein the viscoelastic agent comprises a polymer or polymers selected from the group consisting of:
modified or unmodified sodium hyaluronate, chondroitin sulfate, polyacrylamide carbomers, hydroxypropylmethylcellulose (HPMC), polyvinylpyrrolidone, proteoglycans, collagen, methylcellulose, carboxymethyl cellulose, ethylcellulose, keratin, and combinations thereof.

2. The method of claim 1, wherein the traumatized tissue is middle ear tissue.

3. The method of claim 2, wherein the administration of viscoelastic is made during a surgical procedure.

4. The method of claim 3, wherein the surgical procedure is selected from the group consisting of:
tympanoplasty, mastoidectomy, and ossiculoplasty.

5. The method of claim 4, wherein the viscosity of the agent is greater than 50 Pa.s and the CDI of said agent is greater than zero and less than 10.

6. The method of claim 1, wherein the viscoelastic agent is optionally combined with one or more mucoadhesive polymers selected from the group consisting of polyglycols (hydrogels), chitosan, polycarbophil, hydroxyethyl cellulose, and poloxamer.

7. The method of claim 6, wherein viscosity of the viscoelastic agent or the viscoelastic agent optionally combined with the mucoadhesive polymer is from about 100 Pas to about 8000 Pa.s and wherein the CDI of said viscoelastic agent or the viscoelastic agent optionally combined with the mucoadhesive polymer is from about 2 to about 7.

8. A composition for use in stabilizing delicate tissue, comprising a viscoelastic agent, said viscoelastic agent having a retention ratio (R) greater than 600, a viscosity ($V_0$) of at least 30 Pa.s, and a cohesion-dispersion index (CDI) greater than zero and less than 20, in accordance with the formula:

$$V_0 \times CDI = R;$$

wherein the viscoelastic agent is selected from the group consisting of:
modified or unmodified sodium hyaluronate, chondroitin sulfate, polyacrylamide, carbomers, hydroxypropylmethylcellulose (HPMC), polyvinylpyrrolidone, proteoglycans, collagen, methylcellulose, carboxymethyl cellulose, ethylcellulose, keratin, and combinations thereof.

9. A composition for delivery of a therapeutic agent, comprising a therapeutically effective amount of the therapeutic agent, and a viscoelastic agent, wherein the viscoelastic agent is selected from the group consisting of:
modified or unmodified sodium hyaluronate, chondroitin sulfate, polyacrylamide, carbomers, hydroxypropylmethylcellulose (HPMC), polyvinylpyrrolidone, proteoglycans, collagen, methylcellulose, carboxymethyl cellulose, ethylcellulose, keratin, and combinations thereof, said viscoelastic agent, having a retention ratio greater than 600, a viscosity of at least 30 Pa.s, and a cohesion-dispersion (CDI) greater than zero and less than 20, in accordance with the formula:

$$V_0 \times CDI = R;$$

together with a pharmaceutically acceptable vehicle therefor.

10. The composition of claim 9, wherein the therapeutic agent is selected from the group consisting of: antibiotics, anti-inflammatories, anesthetics, anti-fibrotics, and combinations thereof.

11. The composition of claim 9, wherein the optional mucoadhesive agent is selected from the group consisting of:
polyglycols (hydrogels), chitosan, polycarbophil, hydroxyethyl cellulose, and poloxamer.

12. The method of claim 1, wherein the viscoelastic agent comprises sodium hyaluronate and chondroitin sulfate.

13. The method of claim 12, wherein the sodium hyaluronate has an average molecular weight of about 2.2 million daltons end is present at a concentration of about 1.6% by weight, and wherein the chondroitin sulfate has an average molecular weight of about 50,000 daltons and is present at a concentration of about 4% by weight.

14. The composition of claim 8, wherein the viscoelastic agent comprises sodium hyaluronate and chondroitin sulfate.

15. The composition of claim 14, wherein the sodium hyaluronate has an average molecular weight of about 2.2 million daltons and is present at a concentration of about 1.6% by weight, and wherein the chondroitin sulfate is present at a concentration of about 4% by weight.

16. The composition of claim 9, wherein the viscoelastic agent comprises sodium hyaluronate and chondroitin sulfate.

17. The composition of claim 16 wherein the sodium hyaluronate has an average molecular weight of about 2.2 million daltons and is present at a concentration of about 1.6% by weight, and wherein the chondroitin sulfate is present at a concentration of about 4% by weight.

18. The method of claim 5, wherein the viscosity of the agent is greater than 100 Pa.s, the CDI of the agent is from about 2 to about 7, and the retention factor is from about 600 to about 15,000.

* * * * *